(12) United States Patent
Mulligan et al.

(10) Patent No.: US 11,721,438 B2
(45) Date of Patent: Aug. 8, 2023

(54) INTELLIGENT COLLABORATIVE GENERATION OR ENHANCEMENT OF USEFUL MEDICAL ACTIONS

(71) Applicant: INTERNATIONAL BUSINESS MACHINES CORPORATION, Armonk, NY (US)

(72) Inventors: Natalia Mulligan, Dublin (IE); Marco Luca Sbodio, Dublin (IE); Joao Bettencourt-Silva, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 938 days.

(21) Appl. No.: 16/548,133

(22) Filed: Aug. 22, 2019

(65) Prior Publication Data
US 2021/0057098 A1    Feb. 25, 2021

(51) Int. Cl.
  *G16H 50/20*  (2018.01)
  *G16H 70/20*  (2018.01)
  *G06N 20/00*  (2019.01)
(52) U.S. Cl.
  CPC ............. *G16H 50/20* (2018.01); *G06N 20/00* (2019.01); *G16H 70/20* (2018.01)
(58) Field of Classification Search
  None
  See application file for complete search history.

(56) References Cited

U.S. PATENT DOCUMENTS

| | | | | |
|---|---|---|---|---|
| 2006/0253296 | A1* | 11/2006 | Liisberg | G16H 50/20 |
| | | | | 705/2 |
| 2011/0119212 | A1* | 5/2011 | De Bruin | A61B 5/00 |
| | | | | 706/12 |
| 2014/0188838 | A1* | 7/2014 | Strugov | G06Q 30/0282 |
| | | | | 707/710 |
| 2019/0027257 | A1* | 1/2019 | Ghogawala | G16H 30/40 |
| 2019/0108898 | A1* | 4/2019 | Gulati | G16H 10/60 |
| 2020/0411199 | A1* | 12/2020 | Shrager | G16H 15/00 |
| 2021/0233664 | A1* | 7/2021 | Colley | G16H 20/00 |
| 2022/0139566 | A1* | 5/2022 | Gardina | H04L 9/3213 |
| | | | | 705/2 |

OTHER PUBLICATIONS

B. Eubank et al., "Using the modified Delphi method to establish clinical consensus for the diagnosis and treatment of patients with rotator cuff pathology," BMC Medical Research Methodology, 16: 56. 2016. DOI 10.1186/s12874-016-0165-8.

(Continued)

*Primary Examiner* — Haimei Jiang
(74) *Attorney, Agent, or Firm* — Griffiths & Seaton PLLC

(57) ABSTRACT

Embodiments for intelligent collaborative generation or enhancement of useful medical actions to a user by a processor. One or more useful medical actions may be recommended, with evidence in support thereof, for positively impacting a health state of a user according to data relating to similar users. One or more of the recommended user medical actions may be matched to one or more selected portions of clinical practice guidelines (CPGs). The one or more of the recommended user medical actions may be added as an additional CPG or as an enhancement to one or more of the matching portions of the recommended user medical actions.

18 Claims, 8 Drawing Sheets

(56) References Cited

OTHER PUBLICATIONS

M. Greco, "Democracy-Based Consensus in Medicine," Journal of Cardiothoracic and Vascular Anesthesia, vol. 29, No. 2, 2015, pp. 506-509, https://doi.org/10.1053/j.jvca.2014.11.005.
A. Jackson et al., "Using consensus methods in developing clinical guidelines for exercise in managing persistent low back pain," Physiotherapy, vol. 95, No. 4, 2009, pp. 302-311, ISSN 0031-9406.
B. Kea and B. Sun. "Consensus development for healthcare professionals." Internal and Emergency Medicine, vol. 10,3 (2014): 373-83. doi:10.1007/s11739-014-1156-6.
S. Lewis et al., "Methodologies for the Development of CHEST Guidelines and Expert Panel Reports," Chest, vol. 146, No. 1, 2014, pp. 182-192. https://doi.org/10.1378/chest.14-0824.
L. Wiles et al., "STANDING Collaboration: a study protocol for developing clinical standards," BMJ Open, 2017; 7: e014048. doi: 10.1136/bmjopen-2016-014048.

\* cited by examiner

INTELLIGENT COLLABORATIVE GENERATION OR ENHANCEMENT OF USEFUL MEDICAL ACTIONS

BACKGROUND OF THE INVENTION

Field of the Invention

The present invention relates in general to computing systems, and more particularly to, various embodiments for intelligent collaborative generation or enhancement of useful medical actions by a processor.

Description of the Related Art

In today's society, consumers, business persons, educators, and others use various computing network systems with increasing frequency in a variety of settings. The advent of computers and networking technologies have made possible the increase in the quality of life while enhancing day-to-day activities. For example, many individuals require extensive use of technology relating to the health and the medical field.

Computing systems can include an Internet of Things (IoT), which is the interconnection of computing devices scattered across the globe using the existing Internet infrastructure. IoT devices may be embedded in a variety of physical devices or products. As great strides and advances in technologies come to fruition, the greater the need to make progress in these systems advantageous for efficiency and safety such as, for example, for using the vast amount of available data to recognize impacts on a health state or health of a person.

SUMMARY OF THE INVENTION

Various embodiments for intelligent collaborative generation or enhancement of useful medical actions using one or more processors, are provided. In one embodiment, by way of example only, a method for implementing intelligent collaborative generation or enhancement of useful medical actions, again by a processor, is provided. One or more useful medical actions may be recommended, with evidence in support thereof, for positively impacting a health state of a user according to data relating to similar users. One or more of the recommended user medical actions may be matched to one or more selected portions of clinical practice guidelines (CPGs). Each of the one or more of the recommended user medical actions may be selected and ranked. The one or more of the recommended user medical actions may be added, according to the selecting and ranking, as an additional CPG or as an enhancement to one or more of the matching portions of the recommended user medical actions.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
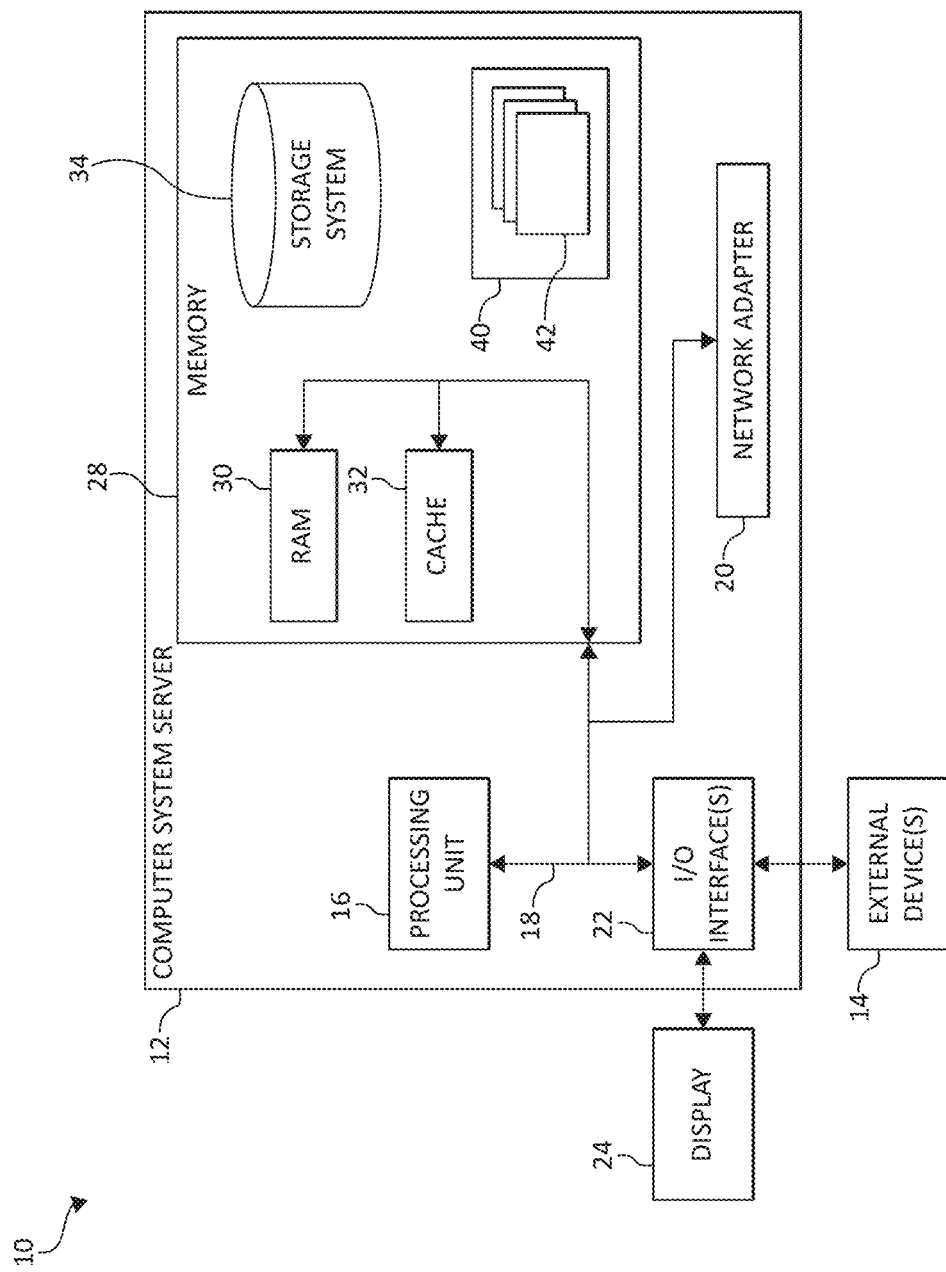
FIG. 1 is a block diagram depicting an exemplary computing node according to an embodiment of the present invention.

As a preliminary matter, computing systems may include large scale computing called "cloud computing," in which resources may interact and/or be accessed via a communication system, such as a computer network. Resources may be software-rendered simulations and/or emulations of computing devices, storage devices, applications, and/or other computer-related devices and/or services run on one or more computing devices, such as a server. For example, a plurality of servers may communicate and/or share information that may expand and/or contract across servers depending on an amount of processing power, storage space, and/or other computing resources needed to accomplish requested tasks. The word "cloud" alludes to the cloud-shaped appearance of a diagram of interconnectivity between computing devices, computer networks, and/or other computer related devices that interact in such an arrangement.

Additionally, the Internet of Things (IoT) is an emerging concept of computing devices that may be embedded in objects, especially appliances, and connected through a network. An IoT network may include one or more IoT devices or "smart devices", which are physical objects such as appliances with computing devices embedded therein. Many of these objects are devices that are independently operable, but they may also be paired with a control system or alternatively a distributed control system such as one running over a cloud computing environment.

The prolific increase in use of IoT appliances in computing systems, particularly within the cloud computing environment, in a variety of settings provide various beneficial uses to a user such as, for example, a medical patient. For example, as the demand for, and access to, data continues to expand in society, consumers of information content, particularly individuals desiring to make well-informed decisions regarding a medical condition or health state of a patient, continue to increase. The openness of the internet, with the ever-increasing availability of a variety of types of computing devices (e.g., IoT devices) and the cloud computing environment for viewing, interacting, or engaging with information, provides the ability of users to have continuous access to information content relating to a variety of settings.

For example, within the health care industry, clinical practice guidelines ("CPGs") may be used by various types of health professionals. In one aspect, evidence-based health care/medicine and evidence-based policies are approaches in the health care industry.

In one aspect, by way of example only, a CPG may be a set of recommendations, actions and goals that support physicians/health care professions making decisions to improve health service delivery and outcomes. In an additional aspect, a CPG may be statements that include recommendations intended to optimize user/patient care that are informed by a systematic review of evidence and an assessment of the benefits and harms of alternative care options. Thus, rather than dictating a one-size-fits-all approach to patient care, a CPG may offer an evaluation of a quality of relevant scientific literature, and an assessment of the likely benefits and harms of a particular treatment. This information enables health care clinicians to select a "best care" or "appropriate care" for a unique patient based on a patient preference.

The CPGs may also include any other evidence-based documents that describe a set of recommendations, instructions or tasks. For example, a local hospital protocol for management of patients with norovirus, a set of recommendations derived from the results of a clinical trial or a research paper with such similar information. A section of a CPG may refer to a particular recommendation or action described in the guideline. A CPG is a collection of multiple recommendations. For example: "measure blood pressure at least once every 12 months" is a recommendation of the Type 2 Diabetes guideline (NICE guideline NG28).

As used herein, the terms "Clinical Practice Guidelines," "Clinical Guidelines," "Guidelines," and "Clinical Pathways" may be used interchangeably. It should be noted, as used herein, the term "patient" may be used interchangeably with the terms "user." The patient profile may include a collection of historical data (e.g., electronic data from one or more electronic health care records) that may be related to one or more medical conditions of a user.

Effective CPG may be used, for example, to: 1) reduce disparities in healthcare delivery (e.g., there may be variabilities between regional and provider-level clinical care leading to poor outcomes and added costs that could be avoided by adhering to one or more CPGs, and 2) reduce the burden that health care professionals currently faces to stay current on, and adhere to, the increasing amounts of medical evidence. Adhering to a CPG may improve healthcare in theory, but guidelines may fail to address local constraints and knowledge (e.g., available in electronic health records (EHRs)). In case of a manual identification process, a use-case may include finding the CPGs describing a healthcare/well-being plan that a specific patient is following. However, such a process is extremely complex as it requires a perfect and complete knowledge of the patient, patient history, and/or other optimal/best clinical practice for all/any conditions. Given that such a perfect and complete knowledge of a patient and complete knowledge of CPGs is rare, only partial knowledge is usually provided or accessible for a patient. Moreover, even when a complete picture of a patient is provided, the coexistence of conditions (chronic and acute) can make the association to one or more sections of CPGs very time consuming and inaccurate. Furthermore, CPGs may include a large number of recommendations in an unstructured form and automatically identify sections of CPGs that are most appropriate for a given patient is currently difficult.

Accordingly, the present invention provides for implementing intelligent collaborative generation or enhancement of useful medical actions (e.g., clinical actions). One or more useful medical actions may be recommended, with evidence in support thereof, for positively impacting a health state of a user according to data relating to similar users. One or more of the recommended user medical actions may be matched to one or more selected portions of CPGs. Each of the one or more of the recommended user medical actions may be selected and ranked. The one or more of the recommended user medical actions may be added, according to the selecting and ranking, as an additional CPG or as an enhancement to one or more of the matching portions of the recommended user medical actions. Thus, intelligent collaborative generation or enhancement of useful medical actions enhance existing CPGs and/or potentially create new CPGs based on recommendations that have been validated collaboratively by domain experts.

In an additional aspect, the present invention provides for collaboratively generating one or more new/additional sections of CPGs, while also enhancing existing sections of clinical guidelines by one or more of the following. First, the present invention provides for recommending the most optimal medical actions ("OMAs") for a patient based on the evidence for similar patients and matching one or more recommended OMAs and the patient profile to existing sections of CPGs. One or more appropriate sections of clinical practice guidelines may be automatically identified for a patient and enabling a domain expert (e.g., a subject matter experts "SMEs") to vote for the recommended OMAs.

In one aspect, the vote of the domain expert may be relative to different dimensions, including, but not limited to, applicability of the recommended OMA (e.g., "yes, I will do that for this patient"), usefulness/effectiveness of the recommended OMA (e.g., "yes, I have done that for this patient, and it was useful/effective). The OMAs may be ranked and/or progressively re-rank based on votes from one or more domain experts (e.g., SMEs), and, based on consensus thresholds operations for example), eventually generate a new section of clinical guideline, or enhance a matching sections of an existing clinical guideline.

In an additional aspect, the present invention may provide for implementing intelligent identification of appropriate sections of clinical practice guidelines. Selected portions of CPGs may be identified for a user according to one or more CPG models and patient pathway models. A Patient Pathway may be a sequential (ordered) set of events and other information that may pertain to a specific condition. A pathway may be associated with at least one episode/encounter and a problem from a problem list. A patient pathway may include a start and end date, which may be the same as condition dates from the problem list. The patient pathway may include an inclusion criteria that may be any discrete event with a date within the patient pathway dates. In one aspect, the patient pathway may be structured into one or more segments. A patient pathway may be generated for each condition in a patient's problem list (e.g., list of all conditions).

For example, the present invention may be employed within healthcare domains such as, for example, Clinical Decision Support Systems ("CDSS"), Computerized Physician Order Entry ("CPOE"), and/or medical/clinical decision making applications. The CDSS may analyze data to support healthcare providers making clinical decisions, including the education of junior clinical staff and evidence based medicine. The CPOE may replace a hospital's paper-based ordering system allowing users to electronically write a full range of orders, maintain an online medication administration record, and review changes made to an order by successive personnel. The CPOE also offers safety alerts that are triggered when an unsafe order (such as for a duplicate drug therapy) is entered, as well as clinical decision support to guide caregivers to less expensive alternatives and/or to clinical choices that better fit established hospital protocols. In one aspect, the medical/clinical decision application includes a cognitive process for selecting one or more courses of action in the context of health or medical diagnosis and treatment.

In an additional aspect, various mechanisms of the illustrate embodiments build a recommendation model by leveraging heterogeneous historical input data about both a single patient and also a population of patients (e.g., a selected number of patients). Such heterogeneous data may also include non-medical data such as, for example, contextual data, social factors, behavior patterns and/or habits, and/or ADLs. In one aspect, the present invention progressively refines the recommendation model by taking into account feedback from one or more domain knowledge experts, a machine learning operation, or a combination thereof. The feedback may include approvals, rejections, and/or rankings of previous recommendations. Thus, the system for intelligent recommendation of usefulness medical actions provides an interactive responsive system that reacts when a domain knowledge expert decides on one or more medical actions for a patient and suggests more optimal alternative when available. A machine learning mechanism may use the heterogeneous historical input and/or feedback information to build the recommendation model and also learn the health state of one or more patients.

In one aspect, the feedback data may also be collected from one or more IoT devices or sensors such as, for example, smart phones, wearable devices or sensors (e.g., proximity sensors, cameras, radio frequency identification "RFID" readers, biometric sensors, wearable sensors, and the like.). Also, as used herein, sensors may include proximity sensors, cameras, radio frequency identification "RFID" readers, biometric sensors, wearable sensors, computers, handheld devices (e.g., Global Positioning System "GPS" device or step counters), smart phones, and/or other sensor based devices.

In an additional aspect, the present invention provides an intelligent medical advice recommendation system. One or more useful medical actions may be recommended at a selected time period for positively impacting a health state of a user according to historical data collected from one or more data sources, one or more user profiles, a domain knowledge, feedback data, a confidence score, or a combination thereof. The medical actions may include a clinical action, nursing activities, patient-care assistance, cleaning actions, actions impacting a health state of the user, or a combination thereof. The one or more useful medical actions may be refined according to the feedback data collected from a machine learning operation, a domain knowledge expert, or a combination thereof.

The term "usefulness" or "useful" as used herein may refer to one or more medical actions having a positive impact upon a patient, one or more medical actions that increases and/or improves a patient's health state, and/or one or more defined purposes, actions, and/or efforts. Useful may be generally defined as the ability to be used for a practical purpose, capable of being put to use, serviceable for an end or purpose, and/or having value or productivity. Useful may also be defined as one or more medical actions that reduce unnecessary, non-useful, unsafe, or ineffective medical actions performed on a patient, reduce an overall cost, and increase productivity of healthcare and/or a health state of a patient. Useful medical actions may also include those medical actions that protect a patient from unnecessary, unsafe, and/or ineffective medical actions.

In one aspect, the health state may include at least one or more medical conditions of one or more users, a health state (e.g., subjective health state "SWB", emotional health state, mental health state, physical health state, or an overall health state) of the one or more users, an emotional state of the one or more users, biometric data, behavior patterns, a health profile of the user, or a combination thereof. In one aspect, health state may be generally described as a normal/standardized or satisfactory condition of existence of the user or a state characterized by health, happiness, emotional stability, mental stability, physical stability, or success. As one of ordinary skill in the art will appreciate, "health state" may be dependent on a number of factors, including such factors as medical condition, emotional stability, mental stability, physical stability, financial stability, a degree or level of happiness, or other factors that may be learned. A health state of a user/patient may be defined. For example, a knowledge base or ontology may be used to define a health state for a user/patient and may include defining and/or indicating one or more correlations between a health state, a plurality of states, medical conditions, activities of daily living (ADL), and context of daily living (CDL).

Moreover, as used herein, ADLs may refer to the most common activities that people perform during a day. For example, activities of daily living may include many activities that take place throughout the day, particularly going to work, child-care, elderly care, health management, communication management, financial management, safety/emergency responses, shopping, visiting friends or family, traveling, housekeeping, grooming or personal hygiene practices, meal preparation/dining out, engaging in social media, and even using a computer. ADLs may also be used in terms of healthcare to refer to the person's daily self-care activities. The context of daily living ("CDL" or "CDLs") may refer to the context in which one or more ADLs are executed or carried out. The CDL may also include one or more dimensions such as, for example, time, location, environment conditions, weather conditions, traffic conditions, and the like. A knowledge domain may provide one or more correlations or relationships between a person's health state and the ADLs and CDLs.

Some ADLs may also be applicable for one or more types of specific events. For example, a person having experienced a recent surgical procedure may require different or altered ADLs for treatment, recovery, or even resuming previously enjoyed ADLs. Each organism (e.g., person) may have different ADLs than other persons. Accordingly, the ADLs for each person may be learned, identified, and analyzed. In one aspect, the ADLs for a person may be learned such as, for example, using machine learning or using a knowledge domain relating to information about the person's activities and behaviors. The machine learning may provide a predictive model that may analyze, determine, identify, and/or predict any ADL behavior or activity for the user.

Accordingly, the "health state" of a particular user may depend greatly upon contextual factors, such as a correlation or relationship between the health state and ADLs/CDLs of the user, and other contextual factors such as defined by a user or learned via artificial intelligence. A deeper, "intellectual" analysis (e.g., artificial intelligence "AI" or machine learning) of the health state of one or more persons (e.g., patients) may be learned based on, for example, standards, rules, practices, and/or learned ADLs, CDLs, and/or other related behaviors or activities. In short, a learning process using AI/machine learning may learn each of the actions, decisions, ADLs, CDLs, behavior patterns of a user, a medical profile (which may include data relating to medical care or medical conditions), or other activities. Each learned health state may be saved as part of a user profile and/or retained in a knowledge domain. For example, the learning may learn preferred ADLs for particular priorities (e.g., brush teeth before leaving to work), preferences (dining at a particular restaurant), or even time periods (e.g., walking to work on warm, sunny days while taking a cab to work on rainy days).

Moreover, as used herein, "best," "appropriate," and/or "optimize" may be used herein interchangeable and refer to and/or defined as "maximize," "minimize," or attain one or more specific targets, objectives, goals, or intentions. "Best," "appropriate," and/or "optimize" may also refer to maximizing a benefit to a user (e.g., maximize a health state/patient profile). "Best," "appropriate," and/or "optimize" may also refer to making the most effective or functional use of a situation, opportunity, or resource.

Additionally, "best," "appropriate," and/or "optimize" may need not refer to a best solution or result but may refer to a solution or result that "is good enough" for a particular application, for example. In some implementations, an objective is to suggest a "best" combination of sections of one or more CPGs, but there may be a variety of factors that may result in alternate suggestion of a combination of sections of one or more CPGs yielding better results. Thus, some changes to the variety of factors may result in a jump from one minimum/maximum to another minimum/maximum. In either case, resulting suggestions of a combination of sections of one or more CPGs may be considered "good enough," "substantially optimal," and/or "sufficiently good." Herein, the terms "best," "appropriate," and/or "optimize" may also refer to such results based on minima (or maxima, depending on what parameters are considered in the optimization problem) for suggesting of a combination of sections of CPGs.

In an additional aspect, the terms "optimize" and/or "optimizing" may refer to an operation performed in order to achieve an improved result such as reduced execution costs or increased resource utilization, whether or not the optimum result is actually achieved. Similarly, the term "optimize" may refer to a component for performing such an improvement operation, and the term "optimized" may be used to describe the result of such an improvement operation.

As used herein, so-called "appropriateness" or "inappropriateness" of sections of one or more CPGs associated with a current patient pathway may be subjective and context dependent. For example, one solution for an appropriate combination of sections of one or more CPGs associated with a current patient pathway may be interpreted and evaluated to be either satisfactory or unsatisfactory depending on one or more contextual factors. Accordingly, the so-called "appropriateness" of a particular combination of sections of one or more CPGs associated with a current patient pathway may depend greatly upon contextual factors, such as a patient profile (e.g., a user profile may include a collection of settings and/or information or attributes with a user such as, for example, gender, weight, age, etc.), environmental factors, social factors, religious factors, cultural factors, and other contextual factors. A deeper, cognitive analysis of the user and CPGs associated with a current patient pathway may be provided to further understand the user and/or interpret the appropriate combination of sections of one or more CPGs associated with a current patient pathway.

It should be noted that reference to calculating an 'interpreted appropriateness" against a predetermined threshold herein following may refer to implementations of a wide variety of metric analysis, data analytics, and other data processing as one of ordinary skill in the art will appreciate. For example, a predetermined threshold may be set as a numerical value, where certain kinds of sections of one or more CPGs associated with a current patient pathway are given certain weighted values, and an aggregate number of the weighted values may be compared against a numerical threshold value.

It should be noted that one or more calculations may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment and/or computing systems associated with one or more medium/means. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
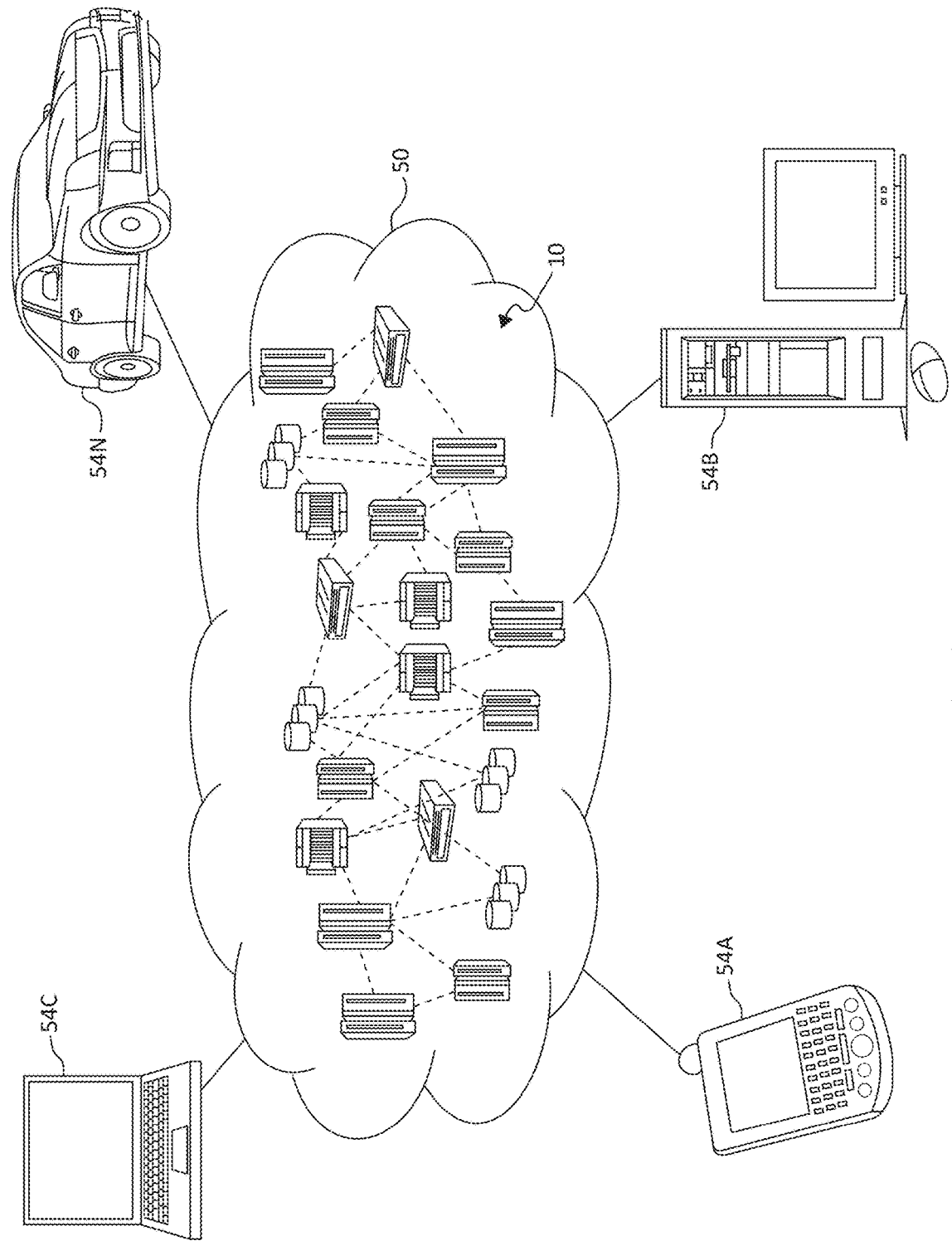
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
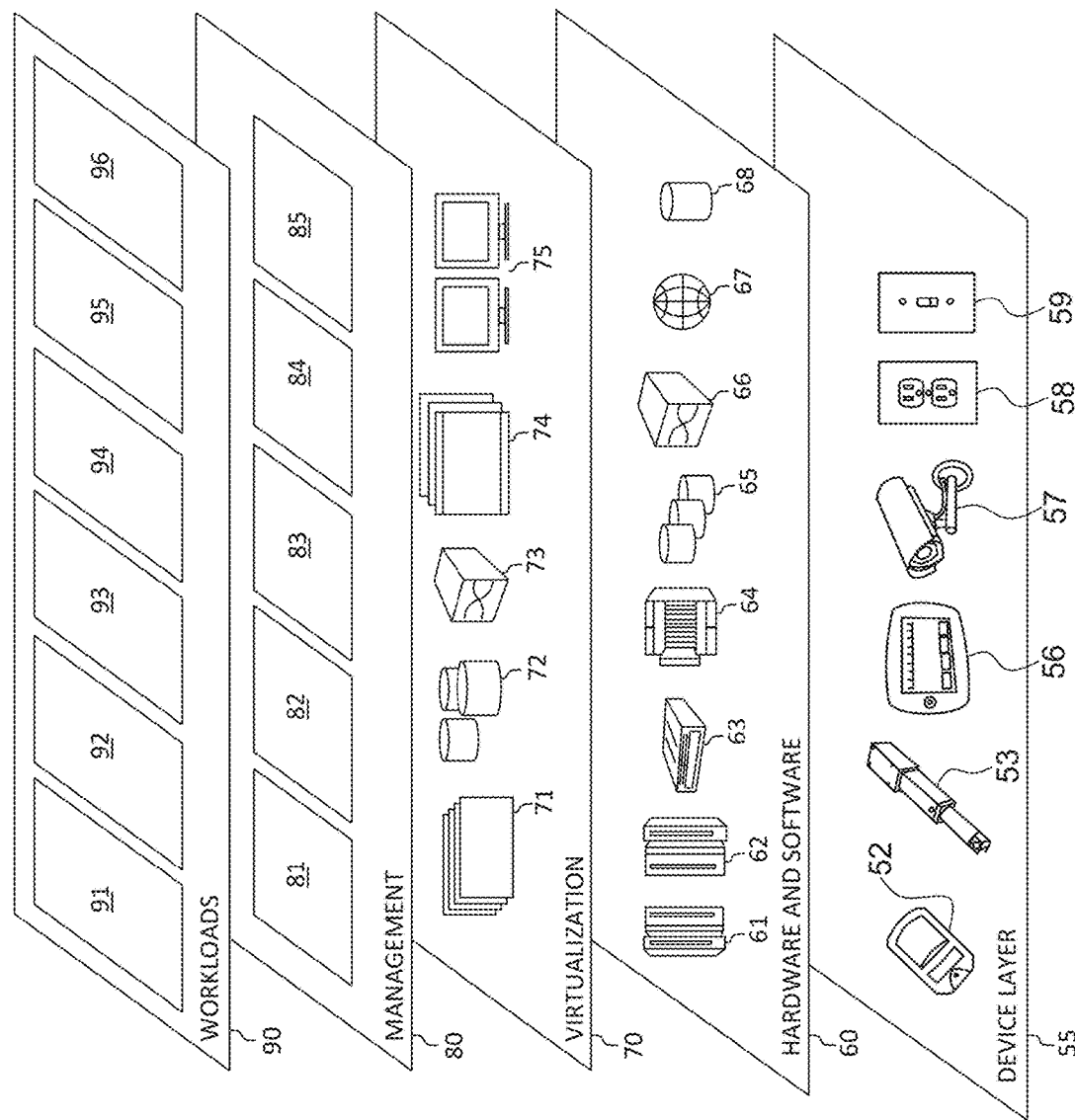
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for intelligent collaborative generation or enhancement of useful medical actions. In addition, workloads and functions 96 for intelligent collaborative generation or enhancement of useful medical actions may include such operations as data analytics, data analysis, and as will be further described, notification functionality. One of ordinary skill in the art will appreciate that the workloads and functions 96 for intelligent collaborative generation or enhancement of useful medical actions may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously mentioned, the mechanisms of the illustrated embodiments provide novel approaches for intelligent collaborative generation or enhancement of useful medical actions. One or more useful medical actions may be recommended, with evidence in support thereof, for positively impacting a health state of a user according to data relating to similar users. One or more of the recommended user medical actions may be matched to one or more selected portions of clinical practice guidelines (CPGs). Each of the one or more of the recommended user medical actions may be selected and ranked. The one or more of the recommended user medical actions may be added, according to the selecting and ranking, as an additional CPG or as an enhancement to one or more of the matching portions of the recommended user medical actions.

In an additional aspect, one or more of the most appropriate sections of CPG that are appropriate for a current patient may be identified. One or more learned machine learning models may be used to match the patient pathway (e.g., ordered sequence of events and other information usually pertaining to a specific medical/clinical condition) to known sections of CPG. In this way, the present invention provides (a) the ability to match sections of CPGs (as opposed to an entire guideline), thus providing fine-grained matching, and (b) the ability to match across CPGs, thus returning a list of sections of CPGs that potentially belong to several different CPG.

In an additional aspect, one or more medical actions may be recommended for impacting a health state of a user according to historical data collected from one or more data sources, one or more user profiles, a domain knowledge, feedback data, or a combination thereof. That is, a set of medical actions (e.g., clinical action) for a patient may be determined maximizing usefulness according to a set of scoring criteria. The medical actions may be determined based on a patient profile, and historical data including different sources (e.g., electronic health record "EMR", habits, activities of daily living, etc.), and based on feedback from domain experts about previous similar cases.

In one aspect, as used herein, the medical actions may include a clinical action (e.g., an observation, diagnosis, and/or treatment of a patient), nursing activities, patient-care assistance, cleaning actions, actions impacting a health state of the user, or a combination thereof. The medical actions may combine medical actions recommended by machine learning and optional medical actions decided by a domain expert. The one or more useful medical actions may be refined according to the feedback data collected from a machine learning operation, a domain knowledge expert, or a combination thereof. Thus, unnecessary, un-useful or unsafe clinical actions performed on patients may be reduced along with reducing an overall cost while increasing productivity of healthcare, and also protecting the patients from unnecessary and unsafe actions.

In one aspect, for recommending the medical actions, the system for intelligent recommendation of useful medical actions includes receiving as input data one or more of the follow. 1) A patient current presentation profile (e.g., the actual symptoms) and/or a set of current or future courses of actions for that patient. 2) A patient clinical history (an EMR, etc.) and social or other relevant contextual history (e.g., ADL, sex, gender, other demographics, social determinants). 3) Historical data of one or more patients and treatments. 4) Historical data of feedback from one or more domain experts (e.g., medial professional such as, a medical doctor, nurse, administer, therapist, hospital staff members, laboratory personnel, etc.) and/or machine learning relating to one or more previous results computed by the intelligent recommendation of useful medical action system in similar cases. 5) A domain knowledge (e.g., a knowledge base/knowledge graphs, clinical documents, scientific literature, guidelines, a list of medications/drugs, side effects of the medications/drugs, clinical/medical research, or other defined data relating to a patient or group of patients). 6) Selected criteria of interest to provide a confidence score each recommendation such as, for example, a cost reduction function, score based on patient safety, or other set of defined criteria or parameters).

Using the input data, for recommending the useful medical actions, the system for intelligent recommendation of useful medical actions includes providing as output one or more recommended medical actions, which may also include a confidence score. In one aspect, the one or more recommended medical actions may be 1) a new recommended clinical action, 2) based on the recommendations of current or future courses of medical actions provided as input (e.g., scored accordingly to its usefulness, safety, cost, etc.). The confidence score may be based on a set of defined criteria indicating a) a level of usefulness the action is for the patient (e.g., treatments, medications, etc.), b) safety levels of the clinical action for a patient (e.g., how safe is the clinical action), c) a cost of the one or more medical actions, and/or a combination of a), b), and c).

Also, evidence data may be provided for each recommended clinical action. The evidence may comprise 1) a set of similar cases from other domain knowledge experts and/or machine learning operations (e.g., provide evidence for training less experienced medical staff), 2) a domain knowledge, and/or 3) historical data. In this way, the system for intelligent recommendation of useful medical actions assists healthcare professionals when dealing with patients, especially when time is critical, by providing real-time advice on usefulness of one or more clinical/medical actions, that may be suggested by medical professionals and/or machine learning, and recommending additional useful actions to reduce the overall cost, improve productivity of healthcare, and also protect the patients from unnecessary and unsafe actions.

Figure 4:
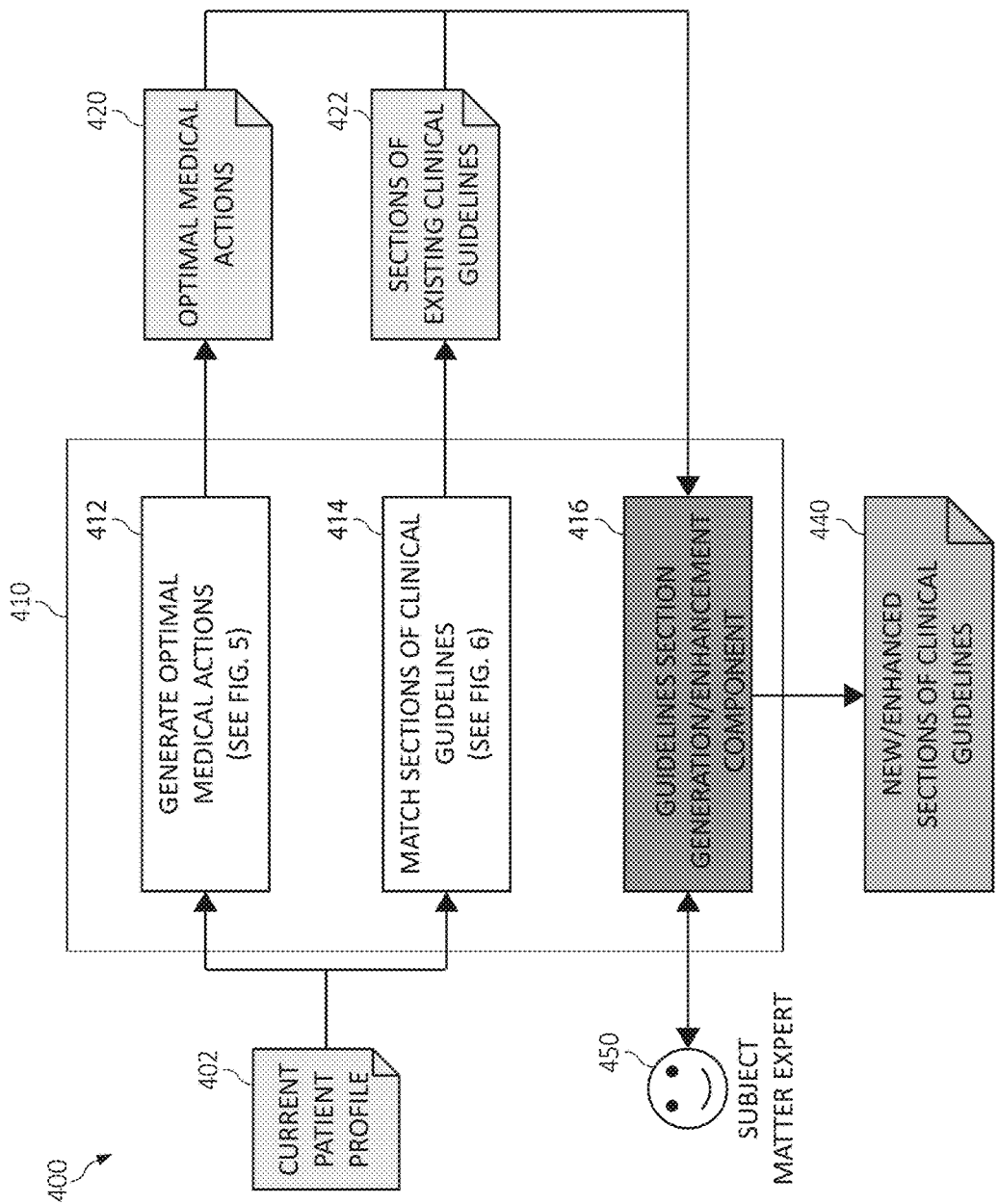
FIG. 4 is an additional block diagram depicting an exemplary functional relationship between various aspects of the present invention.

Turning now to FIG. 4, a block diagram depicting exemplary functional components of computing system 400 according to various mechanisms of the illustrated embodiments is shown. FIG. 4 illustrates intelligent recommendation of useful medical actions workloads and functions and training of a machine-learning model in a computing environment according to an example of the present technology. As will be seen, many of the functional blocks may also be considered "modules" or "components" of functionality, in the same descriptive sense as has been previously described in FIGS. 1-3.

With the foregoing in mind, the module/component blocks of computing system 400 may also be incorporated into various hardware and software components of a system for intelligent recommendation of useful medical actions in accordance with the present invention. Many of the functional blocks 400 may execute as background processes on various components, either in distributed computing components, or on the user device, or elsewhere.

The computing system 400 may include an intelligent collaborative generation or enhancement of useful medical actions service 410. The intelligent collaborative generation or enhancement of useful medical actions service 410 may include a medical actions recommendation component 412, a matching CPGs component 414, and a CPG section generation component 416, each of which may be in association/communication with a patient profile 402 (e.g., a current patient profile), and a domain expert 450.

In one aspect, the intelligent collaborative generation or enhancement of useful medical actions service 410 may provide virtualized computing services (i.e., virtualized computing, virtualized storage, virtualized networking, etc.). More specifically, the intelligent collaborative generation or enhancement of useful medical actions service 410 may provide virtualized computing, virtualized storage, virtualized networking and other virtualized services that are executing on a hardware substrate.

In one aspect, the medical actions recommendation component 412 and the matching CPGs component 414 may receive data relating to the patient profile 402 (e.g., symptoms reported by a patient).

Figure 5:
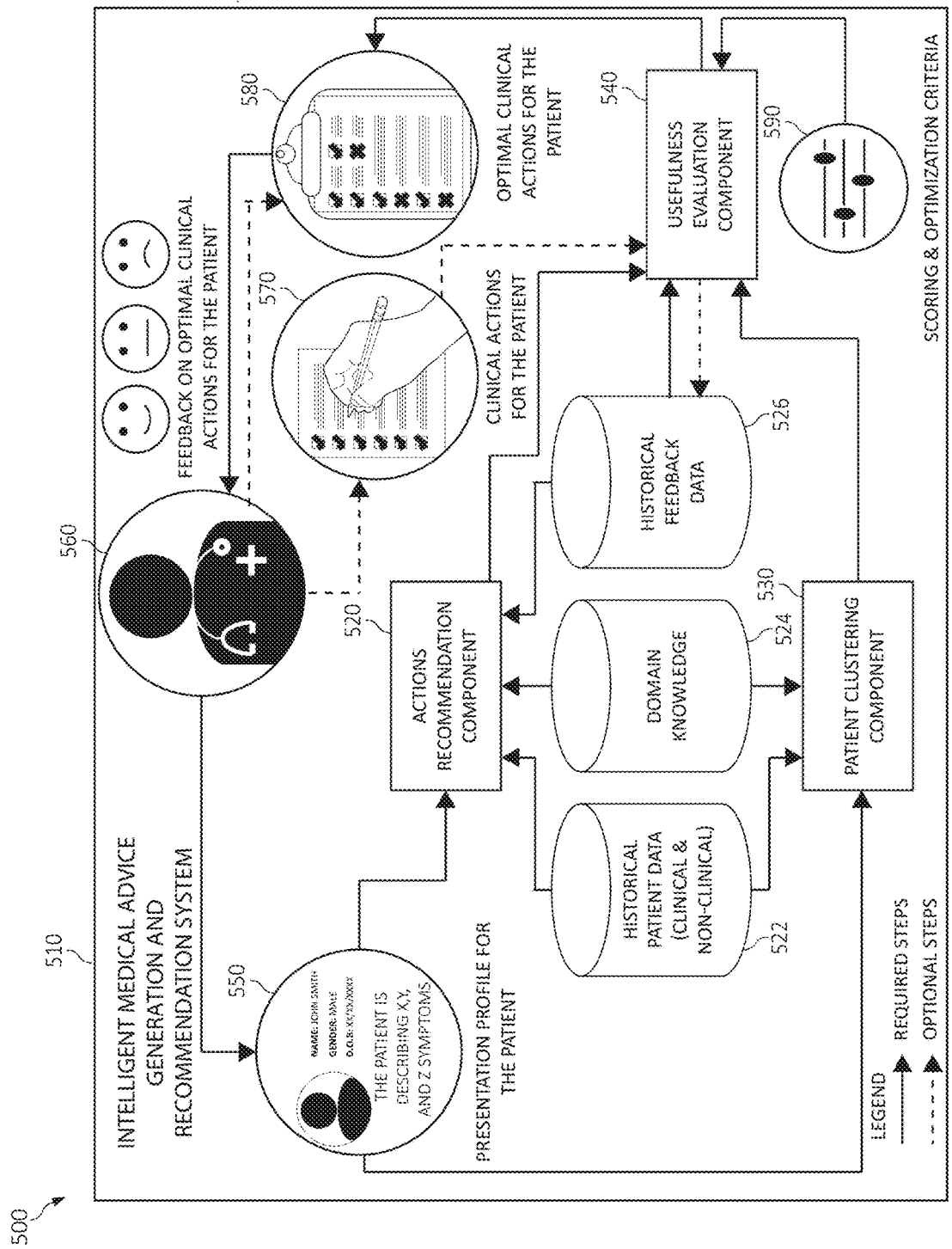
FIG. 5 is an additional flowchart diagram depicting an additional exemplary method for implementing intelligent generation and recommendation of useful medical actions in which aspects of the present invention may be realized.

In one aspect, the medical actions recommendation component 412 may generate and recommend one or more optimal medical actions 420 (e.g., useful/effective medical actions) based on the patient profile 402, which may be described in more detail in FIG. 5. That is, the medical actions recommendation component 412 may generate and recommend one or more optimal medical actions 420, with evidence in support thereof, for positively impacting a health state of the patient profile 402 (e.g., a user) (which may also be optionally based on and/or related to data relating to similar patients (e.g., users)).

Figure 6:
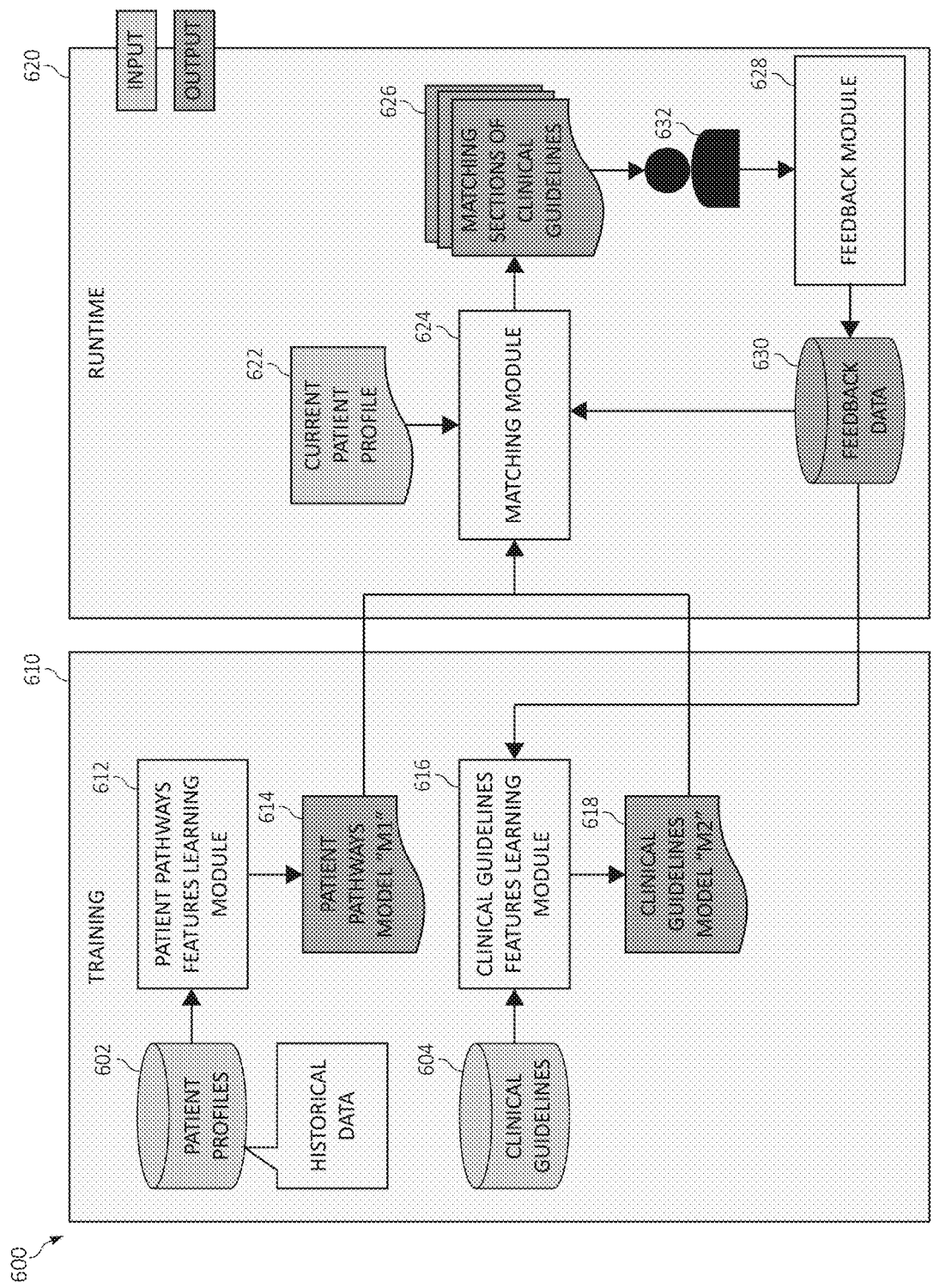
FIG. 6 is an additional flowchart diagram depicting an additional exemplary method for implementing intelligent matching of appropriate sections of clinical practice guidelines by a processor, again in which aspects of the present invention may be realized.

The matching CPGs component 414 may match one or more sections of existing CPGs 422, which is described in more detail in FIG. 6. That is, the medical actions recommendation component 412 may match one or more sections of existing CPGs 422 with the patient profile 402.

Using the optimal medical actions 420 and the one or more sections of existing CPGs 422, the CPG section generation component 416 may match the optimal medical actions 420 to one or more sections of existing CPGs 422 (if any exist). The CPG section generation component 416 may add the optimal medical actions 420 as a new sections of existing CPGs 422 and/or enhance one or more sections of existing CPGs, as in block 440.

In one aspect, the optimal medical actions 420 and the one or more sections of existing CPGs 422 may be text based and text fragments may be converted to term frequency-inverse document frequency ("TF-IDF") vectors where a cosine similarity between the optimal medical actions 420 and the one or more sections of existing CPGs 422 is determined. The cosine similarity among vectors may be used to rank the optimal medical actions 420 and the one or more sections of existing CPGs 422. A predetermined threshold may be used to determine and establish when the optimal medical actions 420 match the one or more sections of existing CPGs 422 (e.g., matching occurs if a matching score exceeds a predetermined threshold).

For example, when the ranking of the optimal medical actions 420 is above predetermined threshold, the optimal medical actions 420 may become and/or added as a new section for a CPG the optimal medical actions 420 if there are no matching SECGs. Alternatively, when the ranking of the optimal medical actions 420 is above predetermined threshold and there are matching SECGs, the optimal medical actions 420 may be added as an enhancement of the matching SECGs. The value of the predetermined threshold may be dynamically learned or updated based on historical data. In another aspect, the ranking score of optimal medical actions 420 may be provided to a selected panel of domain experts (e.g., the domain expert 450) to decide whether or not to promote the optimal medical actions 420.

The CPG section generation component 416 enable (via a user interface "UI" of a computing device) the domain expert 450 to vote on a degree of applicability, a degree of effectiveness, or a combination thereof of the one or more useful medical actions for the user. That is, the CPG section generation component 416 may collect votes from the domain expert 450 about one or more dimensions of the generated optimal medical actions 420 (and potentially matching sections of existing CPGs 422. Based on consensus operation, the CPG section generation component 416 may dynamically rank and/or re-rank the optimal medical actions 420. In one aspect, the consensus may be achieved/reached using one or operations after the votes are collected such as, for example, using a ranking algorithm computes a score based on a confidence interval, using a threshold on the ranking score (when the ranking of an OMA is above that threshold, learning a value of the threshold dynamically based on historical data, or other defined voting operation.

In one aspect, a current patient profile (which may include information for the patient electronic health records, and other sources) may be displayed via the UI. The votes may span different dimensions, and for each dimension, the vote may include either a binary vote (e.g., upvote/downvote) or a discrete vote (e.g., 1 to 5 stars). In one embodiment the domain experts may use binary votes (upvote/downvote) for the following dimensions: the optimal medical actions 420 are appropriate for the current patient, and/or the optimal medical actions 420 yield a positive outcome for the current patient.

Thus, the CPG section generation component 416 may then add the optimal medical actions 420 as the additional CPG upon the ranking score exceeding the predetermined threshold. In an additional aspect, the CPG section generation component 416 may enhance the one or more sections of existing CPGs with the optimal medical actions 420. That is, the one or more sections of existing CPGs may be enhanced with the optimal medical actions 420 matching the one or more sections of existing CPGs upon the ranking score exceeding the predetermined threshold.

Thus, the CPG section generation component 416 performs each of the following: 1) matches OMAs to sections of existing CPGs ("SECGs"), 2) interactively collects votes from domain experts relating to the OMA's and potentially matching SECGs, and 3) ranks the OMAs and when a consensus (between each of the domain experts is achieved such as, for example, a majority vote), the OMA may be promoted as a new section of a CPG if the OMA has no matching SECGs or promoted as an enhancement of one or more matching SECGs if there are matching SECGs.

In one aspect, generating and recommending the optimal medical actions 420 and/or matching the sections of existing CPGs 422, as described herein, may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, back-propagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are within the scope of this disclosure. Also, when deploying one or more machine learning models, a computing device may be first tested in a controlled environment before being deployed in a public setting. Also even when deployed in a public environment (e.g., external to the controlled, testing environment), the computing devices may be monitored for compliance.

In one aspect, the intelligent collaborative generation or enhancement of useful medical actions service 410 may perform one or more calculations according to mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.) Thus, as used herein, a calculation operation may include all or part of the one or more mathematical operations.

Turning now to FIG. 5, a block diagram depicting exemplary functional components 500 according to various mechanisms of the illustrated embodiments is shown. FIG. 5 illustrates intelligent generation and recommendation of useful medical actions workloads and functions and training of a machine-learning model in a computing environment, such as a computing environment 502, according to an example of the present technology. As will be seen, many of the functional blocks may also be considered "modules" or "components" of functionality, in the same descriptive sense as has been previously described in FIGS. 1-4.

With the foregoing in mind, the module/component blocks of computing system 500 may also be incorporated into various hardware and software components of a system for intelligent recommendation of useful medical actions in accordance with the present invention. Many of the functional blocks 500 may execute as background processes on various components, either in distributed computing components, or on the user device, or elsewhere.

The computing system 500 may include an intelligent medical advice generation and recommendation system 510. The intelligent medical advice generation and recommendation system 510 may include an actions recommendation component 520, a patient clustering component 530, and a usefulness evaluation component 540. The actions recommendation component 520, patient clustering component 530, and the usefulness evaluation component 540 may each be in association/communication with historical patient data 522 (e.g., clinical and/or non-clinical data), a domain knowledge 524, and/or historical feedback data 526.

In one aspect, the intelligent medical advice generation and recommendation system 510 may provide virtualized computing services (i.e., virtualized computing, virtualized storage, virtualized networking, etc.). More specifically, the intelligent medical advice generation and recommendation system 510 may provide virtualized computing, virtualized storage, virtualized networking and other virtualized services that are executing on a hardware substrate.

In one aspect, the patient clustering component 530 may receive data relating to a patient presentation profile 550 (e.g., symptoms reported by a patient). The patient clustering component 530 may cluster patients based on named entities extracted from one or more data sources (e.g., a document/text such as notes from care workers) and other structured data (e.g., vitals, gender, age, etc.). In one aspect, the patient clustering component 530 may use a clustering operation such as, for example, K-Means clustering (or a variation thereof), or any other suitable clustering operation. The output patient clustering component 530 may be sent to and/or used by the usefulness evaluation component 540 to identify similar patients and/or (re)rank medical actions based on the cluster.

In one aspect, the actions recommendation component 520 may also receive data relating to the patient presentation profile 550 (e.g., symptoms reported by a patient). The actions recommendation component 520 recommends one or more useful medical actions 580 (e.g., optimal medical actions) based on the patient presentation profile 550. That is, the actions recommendation component 520 cognitively recommend one or more useful medical actions 580 for impacting a health state of a user according to historical data 522 collected from one or more data sources, one or more user profiles (e.g., patient presentation profile 550, the domain knowledge 524, feedback data 526, or a combination thereof.

In one embodiment, the actions recommendation component 520 may use collaborative filtering. The actions recommendation component 520 may be trained on historical data 522 relating to one or more patients (both clinical and nonclinical), and feedback one or more optimal medical actions from the patient from one or more domain knowledge experts 560, which may include a machine learning operation learning the domain knowledge. The actions recommendation component 520 may use the domain knowledge 524 to improve, enhance and/or update the one or more clinical action recommendations.

The usefulness evaluation component 540 may rank and/or re-rank the one or more useful medical actions 580 to maximize a scoring criteria for determining a usefulness of the one or more useful medical actions 580, which a machine learning operation may be used. The machine learning operation may rank a set of medical actions by combining a given collection of ranking or preferences of the medical actions. In one aspect, scoring criteria may include, but not limited, to a determination of how useful and/or necessary an action (e.g., treatment, medication, etc.) based on statistical analysis of historically similar cases, how safe and/or effective an action is on the patient (e.g., action that positively affects the health state of the user) based on patient data and/or the statistical analysis of historically similar cases, and/or a financial cost/constraint of the action is upon the patient. The scoring criteria may be assigned a value such as, for example a percentage and/or a value within a range of values.

In one aspect, if a care worker/medical professional (e.g., domain knowledge expert 560) has provided medical actions 570 as input, the usefulness evaluation component 540 may merge the medical actions 570 provided by the care giver with the useful medical actions 580 determined by the actions recommendation component 520. The ranking of the one or more useful medical actions 580 may be determined and/or computed based on configurable scoring criteria 590, the domain knowledge 524, and feedback data 526 (e.g., historical feedback data) from the domain knowledge experts 560 about previously computed results.

The usefulness evaluation component 540 may use a set of rules to boost medical actions 580 that are more important as compared to other possible medical actions, and to assign a negative score to the one or more useful medical actions 580 that are known to be ineffective and/or unsafe in that particular context. For example, the set of rules may include, but not limited to, assigning a positive, normalized score (e.g., confidence score) to a medical action if the outcome of the medical action applied to previous cases was successful. The confidence score may be increased for those cases having a greater similarity to the user (e.g., a confidence score may have a greater weight, rank, and/or percentage for success on the user).

Turning now to FIG. 6, a block diagram of exemplary functionality 600 of an intelligent matching of appropriate sections of CPGs is depicted. As will be seen, many of the functional blocks may also be considered "modules" or "components" of functionality, in the same descriptive sense as has been previously described in FIGS. 1-5.

As shown, the various blocks of functionality are depicted with arrows designating the blocks' 600 relationships with each other and to show process flow of an intelligent identification of appropriate sections of CPGs. Additionally, descriptive information is also seen relating each of the functional blocks 600. As will be seen, many of the functional blocks may also be considered "modules" or "components" of functionality, in the same descriptive sense as has been previously described in FIGS. 1-6. With the foregoing in mind, the module blocks 600 may also be incorporated into various hardware and software components of a system for image enhancement in accordance with the present invention. Many of the functional blocks 600 may execute as background processes on various components, either in distributed computing components, or on the user device, or elsewhere, and generally unaware to the user performing generalized tasks of the present invention.

As illustrated, the operations for intelligent identification of appropriate existing sections of CPGs may include a training phase 610 and a runtime phase 620.

Starting with block 602, during the training phase, a patient profile may be accessed for a patient having historical data associated therewith. That is, block 602 may include a database with a selected number of historical patient profiles data. The patient profile may be sent to a patient pathways features learning module 612 and used as input. The patient pathways features learning module 612 may learn (and produce as output) one or more models of patient pathways (e.g., patient pathway model "M1"), as in block 614. That is, the patient pathways features learning module 612 may initialize a machine learning operation and implement one or more machine learning operations to learn features of one or more patient pathways. In one aspect, the patient pathways are extracted as an ordered sequence of events from the historical patient profiles data. A neural network may be trained using labeled data that may include 1) a vector representation of patient pathways, and/or 2) labels characterizing the type of pathways. One or more learned patient pathway models may be sent to the matching module 624, for commencing the runtime phase 620.

Additionally, during the training phase 610, a collection of clinical guidelines 604 and/or feedback data 630 (if available from the runtime phase 620) may be sent to the clinical guidelines features learning module 616 and used as input. The clinical guidelines features learning module 616 may learn (and produce as output) one or more clinical guidelines models (e.g., CPG models or clinical guideline model "M2"), as in block 618. In one aspect, the CPGs may be available as documents (e.g., textual data). The clinical guidelines features learning module 616 may build a quantitative representation of each of the features of guidelines. In one embodiment, clinical guidelines features learning module 616 may use artificial intelligence, natural language processing ("NLP), and/or one or more word embedding operations, which yield a vector-based model of the text. Additionally, the clinical guidelines features learning module 616 may use feedback data 630 from one or more domain experts 632 to improve the quality of the learned CPG model. The feedback data 630 may be used as labeled data at training time. The clinical guidelines features learning module 616 may send the one or more models of clinical guidelines (e.g., CPG models or clinical guideline model "M2") to the matching module 624.

In one aspect, the matching module 624 may use as input the patient pathways model M1 (computed during the training phase) and the clinical guidelines model M2 (computed during the training phase). Data from a current patient profile 622 and/or feedback data 630, if available, may also be accessed and used by the matching module 624.

The matching module 624 may compare the data and provide a sorted list of sections of clinical guidelines matching the current patient profile 622. That is, the matching module 624 extracts a patient pathway from the current patient profile 622. For each patient pathway "H", the current patient profile 622 uses the patient pathways model M1 to build a vector representation of patient pathway H. The matching module 624 may determine and/or compute one or more similarity metrics between the vector representation of the patient pathway H and vector representations of the guidelines in clinical guideline model M2. The similarity metric provides a sorted list of sections of guidelines/CPGs that are closest to the patient pathway H. The sections of guidelines/CPGs that are the closest/most similar are the most appropriate/determined section for patient pathway H. If available, the present invention may use the feedback data 630 collected from the domain expert(s) 632 via a feedback module 628 to improve the ranking in the sorted list.

The feedback module 628 may receive as input data from one or more domain experts such as, for example, the domain expert 632, and provide feedback data 630 on the output produced by the matching module 624. That is, the feedback module 628 may provide a structured database of feedbacks. The feedback module 628 allows for users to provide feedback about the matching sections of CPGs using one or more selected/defined user interfaces of a computing system. In one embodiment, the feedback may include, for example, an upvote/downvote to represent agreement/disagreement. The feedback data 630 may also be communicated back to the clinical guidelines features learning module 616 and to the matching module 624.

Figure 7:
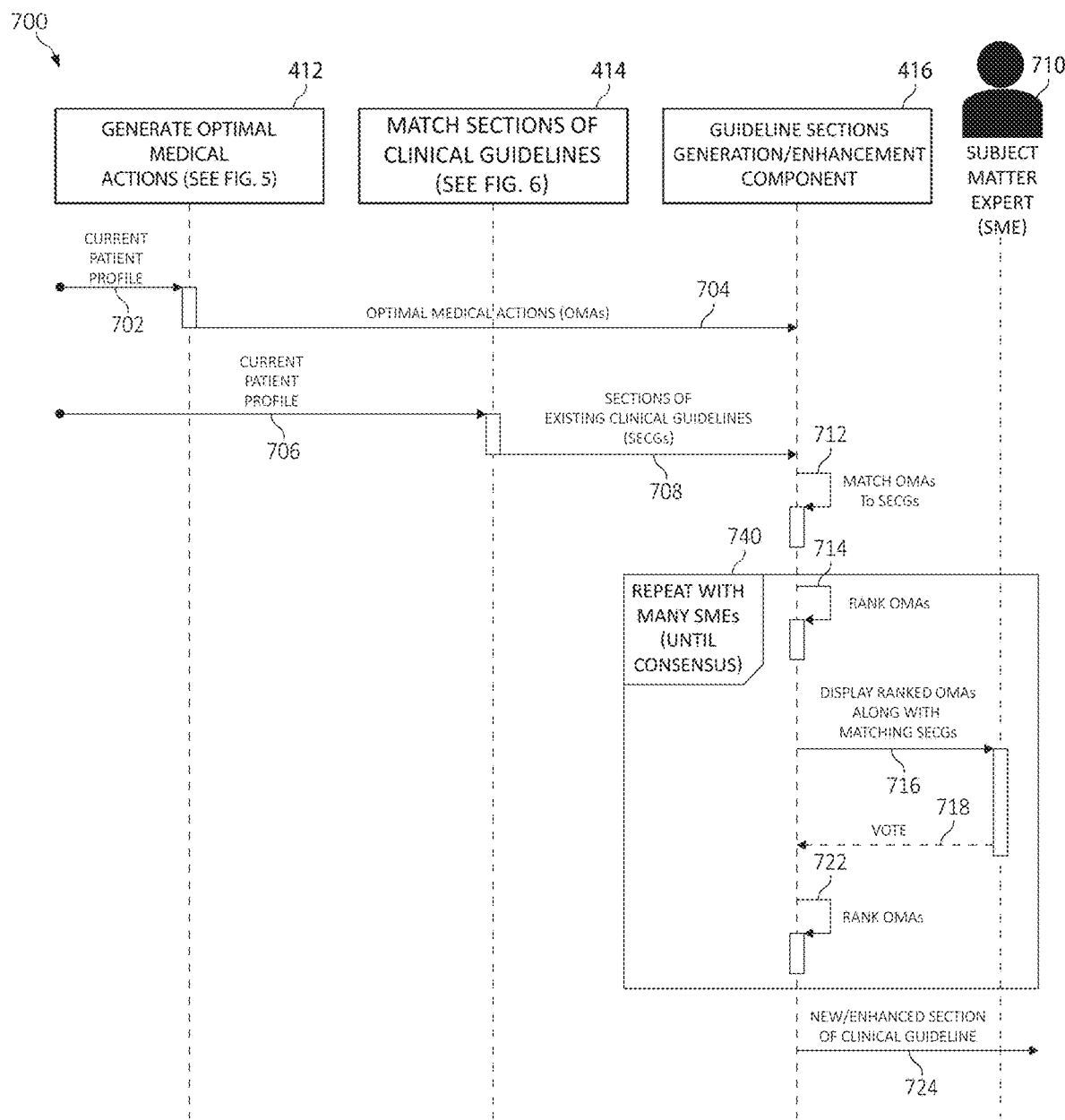
FIG. 7 is an additional flowchart diagram depicting an additional exemplary method for implementing intelligent collaborative generation or enhancement of useful medical actions by a processor in which aspects of the present invention may be realized.

Turning now to FIG. 7, a flow diagram of exemplary functionality 700 of an intelligent collaborative generation or enhancement of useful medical actions is depicted. It should be noted that in the intelligent collaborative generation or enhancement of useful medical actions service 410 of FIG. 4 may be included in and/or associated with computer system/server 12 of FIG. 1, incorporating one or more processing unit(s) 16 to perform various computational, data processing and other functionality in accordance with various aspects of the present invention. For example, functionality 700 of the intelligent collaborative generation or enhancement of useful medical actions service 410 is illustrated using the medical actions recommendation component 412, the matching CPGs component 414, and the CPG section generation component 416.

As shown, the various blocks of functionality are depicted with arrows designating the blocks' 700 relationships with each other and to show process flow of the intelligent collaborative generation or enhancement of useful medical actions service 410. Additionally, descriptive information is also seen relating each of the functional blocks 700. As will be seen, many of the functional blocks may also be considered "modules" or "components" of functionality, in the same descriptive sense as has been previously described in FIGS. 1-6. With the foregoing in mind, the module blocks 700 may also be incorporated into various hardware and software components of a system. Many of the functional blocks 700 may execute as background processes on various components, either in distributed computing components, or on the user device, or elsewhere, and generally unaware to the user performing generalized tasks of the present invention.

Starting with blocks 702 and 706, a current patient profile may be prepared for a patient and sent to both the medical actions recommendation component 412 and the matching CPGs component 414. A list of optimal medical actions ("OMA") may be generated, prepared, and recommended by the medical actions recommendation component 412 for the patient, as in block 704. The current patient profile (e.g., a patient pathway) may be matched to one or more sections of existing CPGs ("SECGs"), as in block 708. The CPG section generation component 416 may match one or more of the OMAs to the SECGs, as in block 712.

Each of the following operations/blocks may be repeatedly executed in block 740 with use of multiple domain experts such as, for example, domain expert 710, until reaching a consensus.

The CPG section generation component 416 may rank the OMAs (e.g., assigning a ranking score), as block 714. The ranked OMAs may be displayed with the matching SECGs via a graphical user interface ("GUI") and/or IoT computing device to a domain expert 710 (e.g., a subject matter expert "SME"), as in block 716. The domain expert(s) 710 may vote on one or more dimensions of the ranked OMAs and/or the matching SECGs, as in block 718. The CPG section generation component 416 may re-rank the OMAs (e.g., updating the ranking score), as block 722.

The CPG section generation component 416 may add the OMAs as one or more new CPG and/or one or more sections of the SECGs may be added with the OMAs, as in block 724. That is, the CPG section generation component 416 may add the OMA's as an additional CPG upon the ranking score exceeding a predetermined threshold, and/or enhancing the matching SECGs with the OMA's matching the one or more selected portions of the matching SECGs upon the ranking score exceeding a predetermined threshold.

It should be noted that the ranking uses and/or leverages (1) clinical and non-clinical historical data about the patient and similar patients, (2) feedback from experts about previous similar cases, and (3) domain knowledge. The historical data may include, for example, electronic health record "EMR", clinical data, historical (non-medical) contextual data (e.g., social data, habits, ADLs, or other non-medical/clinical data). The feedback may be collected from domain knowledge experts (which may include using a machine learning operation to learn the domain knowledge) about previous similar cases of the patient, which may include, for example, acceptance and/or rejection of previous suggestions, scoring of previous suggestions (e.g., 1-5 rating).

Figure 8:
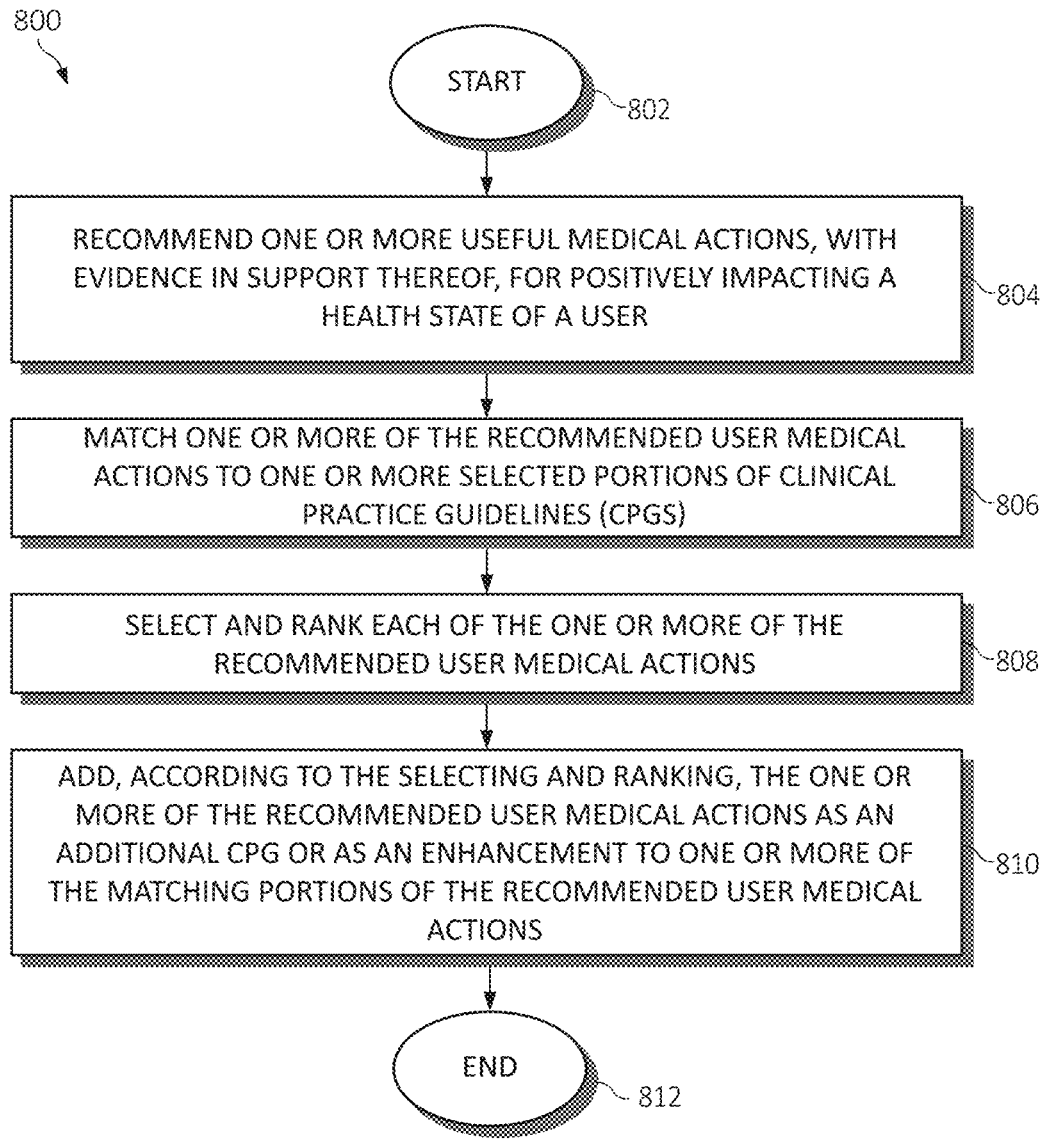
FIG. 8 is an additional flowchart diagram depicting an additional exemplary method for implementing intelligent collaborative generation or enhancement of useful medical actions by a processor, again in which aspects of the present invention may be realized.

Turning now to FIG. 8, a method 800 for implementing intelligent collaborative generation or enhancement of useful medical actions by a processor is depicted, in which various aspects of the illustrated embodiments may be implemented. The functionality 800 may be implemented as a method executed as instructions on a machine, where the instructions are included on at least one computer readable medium or one non-transitory machine-readable storage medium. The functionality 800 may start in block 802.

One or more useful medical actions may be recommended, with evidence in support thereof, for positively impacting a health state of a user, as in block. One or more of the recommended user medical actions may be matched to one or more selected portions of clinical practice guidelines (CPGs), as in block 806. The one or more of the recommended user medical actions may be selected and ranked, as in block 808. The one or more of the recommended user medical actions may be added, according to the selecting and ranking, as an additional CPG or as an enhancement to one or more of the matching portions of the recommended user medical actions, as in block 810. The functionality 800 may end, as in block 812.

In one aspect, in conjunction with and/or as part of at least one block of FIG. 8, the operations of method 800 may include each of the following. The operations of method 800 may provide a list of the one or more selected portions of CPGs belonging to one or more of a plurality of CPGs. The operations of method 800 may include voting on one or more aspects of the one or more useful medical actions according to historical data, selected evidence data, domain experts, a domain knowledge, or a combination thereof. The operations of method 800 may enable one or more domain experts to vote on a degree of applicability, a degree of effectiveness, or a combination thereof of the one or more useful medical actions for the user.

The operations of method 800 may rank or re-rank the one or more useful medical actions according to a scoring criteria, historical data, selected evidence data, domain experts, a domain knowledge, or a combination thereof.

The operations of method 800 may add the one or more useful medical actions as the additional CPG upon a ranking score exceeding a predetermined threshold, and/or enhance the CPGs with the one or more useful medical actions matching the one or more selected portions of the CPGs upon a ranking score exceeding a predetermined threshold. A confidence score may be assigned to the one or more useful medical actions indicating an effectiveness and safety upon the health state of the user (e.g., a positive or negative impact upon the health state of the patient). The operations of method 800 may initialize a machine learning mechanism to learn, identify, and match the one or more useful medical actions and the one or more selected portions of CPGs.

In an additional aspect, the operations of method 800 may also include initializing a machine learning mechanism using the feedback information to learn the health state. The health state may include at least one or more medical conditions, a subjective health state (SWB) of the user, social or contextual data of one or more users, an emotional state of the user, biometric data, behavior patterns, a health profile of the user, or a combination thereof.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for intelligent collaborative generation or enhancement of useful medical actions by a processor, comprising:
   receiving medical and non-medical data associated with both a user and similar users;
   executing machine learning logic to train a recommendation model with the medical and non-medical data;
   recommending one or more useful medical actions, with evidence in support thereof, for impacting a health state of the user according to the recommendation model;
   in conjunction with the recommending, enabling one or more domain experts to vote on a degree of applicability, a degree of effectiveness, or a combination thereof of the one or more useful medical actions for the user, wherein the voting is used as feedback to progressively refine the recommendation model;
   matching the one or more useful medical actions to one or more selected portions of clinical practice guidelines (CPGs); and
   adding the one or more useful medical actions as an additional CPG or as an enhancement according to the matching.

2. The method of claim 1, further including providing a list of the one or more selected portions of CPGs belonging to one or more of a plurality of CPGs.

3. The method of claim 1, further including voting on one or more aspects of the one or more useful medical actions according to historical data, selected evidence data, domain experts, a domain knowledge, or a combination thereof.

4. The method of claim 1, further including ranking or re-ranking the one or more useful medical actions according to a scoring criteria, historical data, selected evidence data, domain experts, a domain knowledge, or a combination thereof.

5. The method of claim 1, further including:
   adding the one or more useful medical actions as the additional CPG upon a ranking score exceeding a predetermined threshold; or
   enhancing the CPGs with the one or more useful medical actions matching the one or more selected portions of the CPGs upon the ranking score exceeding the predetermined threshold.

6. The method of claim 1, further including initializing the machine learning logic to learn, identify, and match the one or more useful medical actions and the one or more selected portions of CPGs.

7. A system for intelligent collaborative generation or enhancement of useful medical actions, comprising:
   one or more computers with executable instructions that when executed cause the system to:
      receive medical and non-medical data associated with both a user and similar users;
      execute machine learning logic to train a recommendation model with the medical and non-medical data;
      recommend one or more useful medical actions, with evidence in support thereof, for impacting a health state of the user according to the recommendation model;
      in conjunction with the recommending, enable one or more domain experts to vote on a degree of applicability, a degree of effectiveness, or a combination thereof of the one or more useful medical actions for the user, wherein the voting is used as feedback to progressively refine the recommendation model;
      match the one or more useful medical actions to one or more selected portions of clinical practice guidelines (CPGs); and
      add the one or more useful medical actions as an additional CPG or as an enhancement according to the matching.

8. The system of claim 7, wherein the executable instructions further provide a list of the one or more selected portions of CPGs belonging to one or more of a plurality of CPGs.

9. The system of claim 7, wherein the executable instructions further vote on one or more aspects of the one or more useful medical actions according to historical data, selected evidence data, domain experts, a domain knowledge, or a combination thereof.

10. The system of claim 7, wherein the executable instructions further rank or re-rank the one or more useful medical actions according to a scoring criteria, historical data, selected evidence data, domain experts, a domain knowledge, or a combination thereof.

11. The system of claim 7, wherein the executable instructions further:
    add the one or more useful medical actions as the additional CPG upon a ranking score exceeding a predetermined threshold; or
    enhance the CPGs with the one or more useful medical actions matching the one or more selected portions of the CPGs upon the ranking score exceeding the predetermined threshold.

12. The system of claim 7, wherein the executable instructions further initialize the machine learning logic to learn, identify, and match the one or more useful medical actions and the one or more selected portions of CPGs.

13. A computer program product for intelligent collaborative generation or enhancement of useful medical actions by a processor, the computer program product comprising a non-transitory computer-readable storage medium having computer-readable program code portions stored therein, the computer-readable program code portions comprising:
    an executable portion that receives medical and non-medical data associated with both a user and similar users;
    an executable portion that executes machine learning logic to train a recommendation model with the medical and non-medical data;
    an executable portion that recommends one or more useful medical actions, with evidence in support thereof, for impacting a health state of the user according to the recommendation model;
    an executable portion that, in conjunction with the recommending, enables one or more domain experts to vote on a degree of applicability, a degree of effectiveness, or a combination thereof of the one or more useful medical actions for the user, wherein the voting is used as feedback to progressively refine the recommendation model;

an executable portion that matches the one or more useful medical actions to one or more selected portions of clinical practice guidelines (CPGs); and an executable portion that adds the one or more useful medical actions as an additional CPG or as an enhancement according to the matching.

14. The computer program product of claim 13, further including an executable portion that provides a list of the one or more selected portions of CPGs belonging to one or more of a plurality of CPGs.

15. The computer program product of claim 13, further including an executable portion that votes on one or more aspects of the one or more useful medical actions according to historical data, selected evidence data, domain experts, a domain knowledge, or a combination thereof.

16. The computer program product of claim 13, further including an executable portion that ranks or re-ranks the one or more useful medical actions according to a scoring criteria, historical data, selected evidence data, domain experts, a domain knowledge, or a combination thereof.

17. The computer program product of claim 13, further including an executable portion that:

adds the one or more useful medical actions as the additional CPG upon a ranking score exceeding a predetermined threshold; or enhances the CPGs with the one or more useful medical actions matching the one or more selected portions of the CPGs upon the ranking score exceeding the predetermined threshold.

18. The computer program product of claim 13, further including an executable portion that initializes the machine learning logic to learn, identify, and match the one or more useful medical actions and the one or more selected portions of CPGs.

* * * * *